United States Patent
Fletcher

(10) Patent No.: US 10,440,916 B2
(45) Date of Patent: Oct. 15, 2019

(54) CANOLA CULTIVAR 15RH0612

(71) Applicant: CARGILL, INCORPORATED, Wayzata, MN (US)

(72) Inventor: Richard Fletcher, Windsor, CO (US)

(73) Assignee: Cargill, Incorporated, Wayzata, MN (US)

( * ) Notice: Subject to any disclaimer, the term of this patent is extended or adjusted under 35 U.S.C. 154(b) by 103 days.

(21) Appl. No.: 15/679,828

(22) Filed: Aug. 17, 2017

(65) Prior Publication Data

US 2018/0064051 A1  Mar. 8, 2018

Related U.S. Application Data

(60) Provisional application No. 62/383,730, filed on Sep. 6, 2016.

(51) Int. Cl.
| | | |
|---|---|---|
| *A01H 5/10* | (2018.01) | |
| *A01H 6/20* | (2018.01) | |
| *A01H 1/02* | (2006.01) | |

(52) U.S. Cl.
CPC .............. *A01H 6/202* (2018.05); *A01H 1/02* (2013.01); *A01H 5/10* (2013.01)

(58) Field of Classification Search
None
See application file for complete search history.

(56) References Cited

U.S. PATENT DOCUMENTS

| | | |
|---|---|---|
| 4,948,811 A | 8/1990 | Lin et al. |
| 5,387,758 A | 2/1995 | Wong et al. |
| 5,434,283 A | 7/1995 | Wong et al. |
| 5,545,821 A | 8/1996 | Wong et al. |
| 5,638,637 A | 6/1997 | Wong et al. |
| 5,861,187 A | 1/1999 | Debonte et al. |
| 5,952,544 A | 9/1999 | Browse et al. |
| 5,965,755 A | 10/1999 | Sernyk et al. |
| 6,051,539 A | 4/2000 | Kodali et al. |
| 6,063,947 A | 5/2000 | Debonte et al. |
| 6,169,190 B1 | 1/2001 | Lanuza et al. |
| 6,291,409 B1 | 9/2001 | Kodali et al. |
| 6,407,317 B2 | 6/2002 | Fan |
| 8,785,731 B2 * | 7/2014 | Kubik ................ A01H 5/10 435/430 |
| 8,981,180 B2 | 3/2015 | Laga et al. |
| 9,920,303 B2 | 3/2018 | Laga et al. |
| 2008/0199587 A1 | 8/2008 | Debonte et al. |
| 2012/0216319 A1 | 8/2012 | Coonrod et al. |
| 2012/0246755 A1 | 9/2012 | Laga et al. |
| 2013/0031678 A1 | 1/2013 | Zheng et al. |
| 2015/0232951 A1 | 8/2015 | Laga et al. |
| 2015/0334976 A1 | 11/2015 | Chungu et al. |

FOREIGN PATENT DOCUMENTS

| | | |
|---|---|---|
| WO | 9306714 A1 | 4/1993 |
| WO | 9950430 A2 | 10/1999 |
| WO | 2011075716 A1 | 6/2011 |
| WO | 2011150028 A2 | 12/2011 |
| WO | 2015077661 A1 | 5/2015 |
| WO | 2018031293 A1 | 2/2018 |

* cited by examiner

*Primary Examiner* — Elizabeth F McElwain

(57) ABSTRACT

This invention relates to a canola hybrid cultivar designated 15RH0612 that includes plants, DNA, and seeds of canola 15RH0612. Methods for producing canola plants, such as canola plant varieties, hybrid canola plants, or other canola plants, as by crossing canola 15RH0612 with itself or any different canola plant are also part of this invention as are the resultant canola plants including the plant parts and seeds.

17 Claims, No Drawings

CANOLA CULTIVAR 15RH0612

This application claims the benefit of U.S. Provisional Patent Application, Ser. No. 62/383,730, filed, Sep. 6, 2016, entitled "CANOLA CULTIVAR 15RH0612", which application is hereby incorporated by reference in its entirety.

FIELD OF THE INVENTION

This invention relates to a canola hybrid cultivar designated 15RH0612 that includes plants, DNA, and seeds of canola 15RH0612. Methods for producing canola plants, such as canola plant varieties, hybrid canola plants, or other canola plants, as by crossing canola 15RH0612 with itself or any different canola plant are also part of this invention as are the resultant canola plants including the plant parts and seeds. This invention further relates to methods for producing 15RH0612 derived canola plants and to methods for regenerating such plants from tissue cultures of regenerable cells as well as the plants obtained therefrom. Methods for producing a canola plant from 15RH0612 containing in its genetic material one or more transgenes and to the transgenic canola plants produced by that method are also part of this invention.

BACKGROUND OF THE INVENTION

"Canola", refers to a particular class of rapeseed (*Brassica napus oleifera annua*) having: (i) a seed oil that contains less than 2% erucic acid, and (ii) an oil-free meal that contains less than 30 micromoles aliphatic glucosinolates per gram of meal. Canola seed can be extracted or pressed for cooking oil and the residual meal is used as an organic fertilizer and as a high-protein animal feed supplement. Industrial uses of canola include biodiesel and plastic feedstocks.

Farmers in Canada began producing canola oil in 1968. Early canola cultivars were known as single zero cultivars because their oil contained 5% or less erucic acid, but the glucosinolates content was still higher than desired. In 1974, the first licensed double zero cultivars (low erucic acid and low glucosinolates) were grown. All current canola cultivars are double zero cultivars.

Because the fatty acid profile of canola oil is generally viewed as "healthy", its use is rising steadily both as an oil for cooking and as an ingredient in processed foods. It is generally lower in saturated fatty acids and high in mono-unsaturated fatty acids than other seed oils. In addition, many people prefer the light color and mild taste of canola oil over other oils that contain monounsaturated fatty acids.

The goal of a canola breeder is to develop new, unique, and superior canola cultivars having improved desirable traits. Improved performance is manifested in many ways. Higher yields of canola plants contribute to higher seed production per acre, a more profitable agriculture and a lower cost of products for the consumer. Improved oil profiles and quality of resulting oil is an important factor in the development of new canola cultivars. Adapting canola plants to a wider range of production areas achieves improved yield and vegetative growth. Improved plant uniformity enhances the farmer's ability to mechanically harvest canola. Improved nutritional quality increases its value in food and feed.

The development of new cultivars in a canola plant breeding program involves numerous steps, including: (1) selection of parent canola plants for the initial breeding crosses; (2) producing and selecting inbred breeding lines and cultivars by either the doubled-haploid method or repeated generations of selfing individual plants; (3) producing and selecting hybrid cultivars by crossing a selected inbred male-sterile line with an unrelated inbred restorer line to produce the F1 hybrid progeny having restored vigor; and (4) thoroughly testing these advanced inbreds and hybrids compared to appropriate standards for three or more years in environments representative of the commercial target areas.

Development and selection of new canola parental lines, the crossing of these parental lines, and selection of superior hybrid progeny are vital to maintaining a canola breeding program. The F1 hybrid canola seed is produced by manual crosses between selected male-fertile parents or by using male-sterility systems. These hybrids are selected for certain single-gene or multiple gene traits. Additional data on parental lines, as well as the phenotype of the hybrid, influence the breeder's decision whether to continue with the specific hybrid cross.

The method of doubled-haploid breeding consists of donor selection, microspore culture and chromosome doubling, embryo cold stress, plantlet regeneration, ploidy analysis, and self-pollination to produce seed of doubled-haploid lines. The advantage of the doubled-haploid method is that the time to develop a new completely homozygous and homogeneous cultivar can be reduced by 3 years compared to the conventional inbreeding method of multiple generations of self-pollination.

These processes, which lead to the final step of marketing and distribution of a cultivar, usually take from 8 to 12 years from the time the parental cross is made. Therefore, development of new canola inbred and hybrid cultivars is a slow, costly process that requires the resources and expertise of plant breeders and numerous other specialists.

It is nearly impossible for two canola breeders to independently develop genetically-identical canola inbreds or hybrids expressing all the same trait characteristics. The cultivars that are developed cannot be predicted because the breeder's selection occurs in unique environments, with no control over meiotic genetic recombination (using conventional breeding procedures), and with millions of different possible genetic combinations possible. A breeder of ordinary skill in the art cannot predict the final resulting lines he/she develops, except possibly in a very gross and general fashion. It is unlikely a breeder could produce the same cultivar twice by using the exact same original parents and the same selection techniques.

Canola cultivars and other sources of canola germplasm are the foundation material for all canola breeding programs. Despite the existence and availability of numerous canola cultivars and other source germplasm, a need still exists for the development of improved germplasm to improve and maximize yield and oil quality.

The foregoing examples of the related art and limitations related therewith are intended to be illustrative and not exclusive. Other limitations of the related art will become apparent to those of skill in the art upon a reading of the specification.

SUMMARY OF THE INVENTION

According to the invention, there is provided a novel canola cultivar designated 15RH0612. This invention thus relates to the seeds of canola 15RH0612, to the plants, or plant parts, of canola 15RH0612 and to methods for producing a canola plant produced by crossing the canola 15RH0612 with itself or another canola cultivar, and the creation of variants by mutagenesis or transformation of canola 15RH0612.

Thus, any such methods using the canola 15RH0612 are part of this invention: selfing, backcrossing, hybrid production, crossing to populations, and the like. All plants produced using canola 15RH0612 as a parent, are within the scope of this invention. Advantageously, the canola 15RH0612 could be used in crosses with other, different, canola plants to produce first generation (F1) canola hybrid seeds and plants with superior characteristics.

In another aspect, the present invention provides for single or multiple gene-converted plants of canola 15RH0612. The transferred gene(s) may preferably have dominant or recessive allele(s). Preferably, the transferred gene(s) will confer such traits as herbicide resistance, insect resistance; resistance to bacterial, fungal, or viral disease; male fertility, male sterility, enhanced nutritional quality, or industrial usage. The gene may be a naturally occurring canola gene or a transgene introduced through genetic engineering techniques.

In another aspect, the present invention provides regenerable cells for use in tissue culture of canola 15RH0612. The tissue culture will preferably be capable of regenerating plants having the physiological and morphological characteristics of the foregoing canola plant, and of regenerating plants having substantially the same genotype as the foregoing canola plant. Preferably, the regenerable cells in such tissue cultures will be embryos, protoplasts, meristematic cells, callus, pollen, leaves, anthers, roots, root tips, flowers, seeds, pods or stems. Still further, the present invention provides canola plants regenerated from the tissue cultures of the invention.

In another aspect, the present invention provides a method of introducing a desired trait into canola 15RH0612 wherein the method comprises: crossing a 15RH0612 plant with a plant of a different canola genotype that comprises a desired trait to produce F1 progeny plants, wherein the desired trait is selected from the group consisting of male sterility, herbicide resistance, insect resistance, and resistance to bacterial disease, fungal disease or viral disease; selecting one or more progeny plants that have the desired trait to produce selected progeny plants; crossing the selected progeny plants with the 15RH0612 plants to produce backcross progeny plants; selecting for backcross progeny plants that have the desired trait and physiological and morphological characteristics of canola 15RH0612 to produce selected backcross progeny plants; and repeating these steps to produce selected first or higher backcross progeny plants that comprise the desired trait and all of the physiological and morphological characteristics of canola 15RH0612. Included in this aspect of the invention is the plant produced by the method wherein the plant has the desired trait and all of the physiological and morphological characteristics of canola 15RH0612.

In addition to the exemplary aspects and embodiments described above, further aspects and embodiments will become apparent by study of the following descriptions.

DETAILED DESCRIPTION OF THE INVENTION

In the description and examples that follow, a number of terms are used. To provide a clear and consistent understanding of the specification and claims, including the scope to be given such terms, the following definitions are provided.

Definitions of Plant Characteristics

Backcrossing: A process in which a breeder repeatedly crosses hybrid progeny back to one of the parents; for example, a first generation hybrid F1 crossed back to one of the parental genotypes of the F1 hybrid.

Cultivar: A plant genotype that has been intentionally bred or selected to be genetically distinct, uniform, and stable, and is maintained through cultivation or other propagation.

Days to Flowering: The number of days from planting to the stage when 50% of the plants show one or more open flowers.

Days to Bolting: The number of days from planting to the appearance of an elongating vegetative stem with a floral bud.

Days to Last Flower: The number of days from planting to when all of the flowers on a plant have opened.

Glyphosate Herbicide Resistance: Resistance of a plant to the action of glyphosate; conferred in crops by genetic transformation of the crop plant using a 5-enol-pyruvylshikimate-3-phosphate synthase (EPSPS) gene that is insensitive to the effect of glyphosate, or a bacterial glyphosate oxidoreductase (GOX) gene that cleaves the nitrogen-carbon bond in glyphosate yielding aminomethylphosphonic acid.

Herbicide Resistance: When a plant has negligible effect from contact with an herbicide because the plant does not take up the herbicide or sequesters the herbicide in a manner that renders it harmless.

Herbicide Tolerance: When a plant has negligible effect from contact with an herbicide because the plant metabolically detoxifies the herbicide.

Hybrid: A cultivar or plant-breeding progeny based upon the controlled cross-pollination between or among distinct parent lines, so that the resulting seed inherits its genetic composition from those parent lines. Seed for a particular hybrid can be repeatedly and predictably produced when repeatedly making controlled cross-pollinations from the same stable female and male parent genotypes.

Inbred: A relatively stable plant genotype resulting from doubled haploids, successive generations of controlled self-pollination, successive generations of controlled backcrossing to a recurrent parent, or other method to develop homozygosity.

Linoleic Acid: means a (C18:2) fatty acid.
Linolenic Acid: means a (C18:3) fatty acid.
Oleic Acid: means a (C18:1) fatty acid.
Palmitic Acid: means a (C16:0) fatty acid.
Seed Weight: The weight in grams of 1000 seeds at maturity at 5% to 6% moisture.
Stearic Acid: means a (C18:0) fatty acid.
Total Saturates: means the combination of the percentages of the following fatty acids which may be present in canola oils. Total Saturates refers to the total of myristic acid (C14:0), palmitic acid (C16:0), stearic acid (C18:0), arachidic acid (C20:0), behenic acid (C22:0), and lignoceric acid (C24:0).
Yield: means quantity of grain produced in grams per plant.

Description of 15RH0612

Canola 15RH0612 is a hybrid cultivar produced from a cross between proprietary Cargill canola inbreds 14CA3082.30 and 14RR5004.72.0075.

Canola 15RH0612 has resistance to the herbicide glyphosate. Fields of canola are subject to a wide variety of weedy species, including volunteer plants from a previous crop, which can affect the oil profile of the harvested crop. Use of a glyphosate herbicide in a canola hybrid crop that has glyphosate herbicide resistance provides broad-spectrum control of weedy species in that crop. The glyphosate herbicide resistance in canola 15RH0612 provides an effective means to maintain the integrity of the desired harvested oil profile of a hybrid crop derived from canola 15RH0612 by reducing the contamination of seed from volunteer plants and weedy species that are not easily separated from the harvested canola grain within commercial production.

The cultivar 15RH0612 has shown uniformity and stability of characteristics over multiple generations of testing. The production parents have been self-pollinated and can be increased through multiple generations with careful attention to uniformity of plant type for the parent lines and consequently for 15RH0612.

The present invention relates to a canola plant that expresses substantially all of the physiological and morphological characteristics of cultivar 15RH0612. Any plants produced from cultivar 15RH0612 are contemplated by the present invention and are, therefore, within the scope of this invention. A description of morphological and other characteristics of cultivar 15RH0612 are presented in Table 1.

TABLE 1

Morphological and Other Characteristics of Canola *Brassica napus* 15RH0612

| Characteristic | Value (variance) |
|---|---|
| Season Type (Spring, Winter) | Spring |
| Type of Cultivar | Hybrid |
| Days to Bolting | 43.56 (5.00) |
| Days to Flower | 53.33 (7.81) |
| Days to Last Flower | 78.22 (13.14) |
| Harvest Index | 0.12 (0.02) |
| Yield (g) per plant | 2.86 (0.55) |
| Seed Weight | 3.46 (0.33) |

Canola oils produced from 15RH0612 are particularly useful for frying applications. The major challenges faced by fast food restaurants in frying involves the desire to have a good tasting oil that is also stable to the intense high heat and moisture inherent in frying conditions. Coupled with those challenges is the desire to have oils that are also reduced in saturated fatty acids. Fully saturated fats, either naturally occurring or produced through hydrogenation of other oils have excellent stability, however, these oils are viewed negatively by the public. The oils of 15RH0612 were developed to address the three pronged need for a frying oil to be stable, great tasting, and low in total saturates. Stability is achieved by maintaining a low content of linolenic acid (C18:3). This fatty acid is particularly susceptible to oxidation in the frying environment. Flavor is maintained by keeping a high content of linoleic acid (C18:2). Finally, the customer awareness around saturated fat is managed by having an oil with less than 5% total saturates. All three of these important parameters had never been achieved in canola crop. Accordingly, oils of 15RH0612 can be used produce fried foods such as snack chips (e.g., corn or potato chips), french fries, or other quick serve foods.

In addition, canola hybrid 15RH0612 has exhibited a unique and valuable fatty acid profile in the oil extracted from it mature seeds grown in field trials at various locations. Oil characteristics are set out in Table II below.

TABLE II

| Cultivar | % C18: 1 (min, max) | % C18: 2 | % C18: 3 | % Total Sats |
|---|---|---|---|---|
| 15RH0612 | 66.53 (59.9, 69.8) | 24.09 (21.1, 30.6) | 2.50 (2.0, 3.1) | 4.42 (4.0, 5.6) |

15RH0612 and any cultivar derived from 15RH0612 as contemplated herein may have a C18:3 level in the canola seed or oil of between 2.0% and 3%. Additional embodiments have levels from i) 2.0% to 2.5%; ii) 2.0% to 2.5%; or iii) 2.0% to 3.1%.

15RH0612 and any cultivar derived from 15RH0612 as contemplated herein may have a C18:2 linoleic acid level in the canola seed or oil of greater than 20% or 21%. Additional embodiments have levels from i) 21% to 28%; ii) 24% to 26%; iii) 21.1% to 28.8%; or iv) 21.1% to 30.6%.

15RH0612 and any cultivar derived from 15RH0612 as contemplated herein may have a C18:1 oleic acid level in the canola seed or oil of greater than 60% or 65%. Additional embodiments have levels from i) 60% to 70%; ii) 63% to 68%; or iii) 59.9% to 69.8%.

15RH0612 and any cultivar derived from 15RH0612 as contemplated herein have a total saturates level of less than 5%. Commodity canola oils commonly used in industry and by consumers have a saturate levels of between 6-8%. See, e.g., *Bailey's Industrial Oil and Fat Products*, Section 2.2, "Canola Oil" on pages 61-121 of Volume 2 (6th Edition, 2005). Embodiments of the present invention have total saturates level in the canola seed or oil of between 3.5% and 5%. Additional embodiments have levels from i) 4% to 5%; ii) 4 to 4.5%; iii) 4.2% to 4.7%; and iv) 4.0% to 5.6%.

The fatty acid composition of oil obtained from seed of *Brassica* plants can be determined by methods well known in the art. Typically it can be determined by first crushing and extracting oil from seed samples (e.g., bulk seed samples of 10 or more seeds). TAGs in the seed are hydrolyzed to produce free fatty acids, which then can be converted to fatty acid methyl esters and analyzed using techniques known to the skilled artisan, e.g., gas-liquid chromatography (GLC) according to AOCS Procedure Ce 1-62. Near infrared (NIR) analysis can be performed on whole seed according to AOCS Procedure Am-192 (revised 1999). Numerical values presented herein are a weight percentage. The percentage of a particular fatty acid is described as a percentage of the total fatty acids in the sample as identified empirically.

This invention is also directed to methods for producing a canola plant by crossing a first parent canola plant with a second parent canola plant, wherein the first or second canola plant is a canola plant from 15RH0612. Further, both first and second parent canola plants may be from 15RH0612. Therefore, any methods using 15RH0612 are part of this invention: selfing, backcrosses, hybrid breeding, and crosses to populations. Any plants produced using 15RH0612 as parents are within the scope of this invention.

Tissue Culture of Canola

Further production of the 15RH0612 can occur by self-pollination or by tissue culture and regeneration. Tissue culture of various tissues of canola and regeneration of plants therefrom is known. For example, the propagation of a canola cultivar by tissue culture is described in any of the following but not limited to any of the following: Chuong et al., "A Simple Culture Method for *Brassica* hypocotyls Protoplasts," *Plant Cell Reports* 4:4-6 (1985); Barsby, T. L., et al., "A Rapid and Efficient Alternative Procedure for the Regeneration of Plants from Hypocotyl Protoplasts of *Brassica napus*," *Plant Cell Reports* (Spring, 1996); Kartha, K., et al., "In vitro Plant Formation from Stem Explants of Rape," *Physiol. Plant*, 31:217-220 (1974); Narasimhulu, S., et al., "Species Specific Shoot Regeneration Response of Cotyledonary Explants of *Brassicas*," *Plant Cell Reports*

(Spring 1988); Swanson, E., "Microspore Culture in *Brassica,*" *Methods in Molecular Biology*, Vol. 6, Chapter 17, p. 159 (1990).

Further reproduction of the variety can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybeans," *Crop Sci.* 31:333-337 (1991); Stephens, P. A., et al., "Agronomic Evaluation of Tissue-Culture-Derived Soybean Plants," *Theor. Appl. Genet.* (1991) 82:633-635; Komatsuda, T. et al., "Maturation and Germination of Somatic Embryos as Affected by Sucrose and Plant Growth Regulators in Soybeans Glycine gracilis Skvortz and Glycine max (L.) Merr." *Plant Cell, Tissue and Organ Culture,* 28:103-113 (1992); Dhir, S. et al., "Regeneration of Fertile Plants from Protoplasts of Soybean (Glycine max L. Merr.); Genotypic Differences in Culture Response," *Plant Cell Reports* (1992) 11:285-289; Pandey, P. et al., "Plant Regeneration from Leaf and Hypocotyl Explants of Glycine-wightii (W. and A.) VERDC. var. longicauda," *Japan J. Breed.* 42:1-5 (1992); and Shetty, K., et al., "Stimulation of In Vitro Shoot Organogenesis in Glycine max (Merrill.) by Allantoin and Amides," *Plant Science* 81:245-251 (1992). The disclosures of U.S. Pat. No. 5,024,944 issued Jun. 18, 1991 to Collins et al., and U.S. Pat. No. 5,008,200 issued Apr. 16, 1991 to Ranch et al., are hereby incorporated herein in their entirety by reference. Thus, another aspect of this invention is to provide cells which upon growth and differentiation produce canola plants having the physiological and morphological characteristics of canola 15RH0612.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, describe certain techniques, the disclosures of which are incorporated herein by reference.

Single-Gene Converted (Conversion) Plants

When the term "canola plant" is used in the context of the present invention, this also includes any single-gene conversions of that variety. The term "single-gene converted plant" as used herein refers to those canola plants that are developed by a plant breeding technique called backcrossing, or via genetic engineering, wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental canola plant that contributes the gene for the desired characteristic is termed the "non-recurrent" or "donor parent." This terminology refers to the fact that the non-recurrent parent is used one time in the backcross protocol and therefore does not recur. The parental canola plant to which the gene or genes from the non-recurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (non-recurrent parent) that carries the single gene of interest to be transferred. The resulting progeny from this cross are then crossed again to the recurrent parent and the process is repeated until a canola plant is obtained wherein essentially all of the desired morphological and physiological characteristics of the recurrent parent are recovered in the converted plant, in addition to the single transferred gene from the non-recurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the non-recurrent parent, while retaining essentially all of the rest of the desired genetic, and therefore the desired physiological and morphological, constitution of the original variety. The choice of the particular non-recurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single-gene traits have been identified that are not regularly selected for in the development of a new variety but that can be improved by backcrossing techniques. Single gene traits may or may not be transgenic, examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these single-gene traits are described in U.S. Pat. Nos. 5,959,185, 5,973,234 and 5,977,445, the disclosures of which are specifically hereby incorporated by reference.

This invention also is directed to methods for producing a canola plant by crossing a first parent canola plant with a second parent canola plant wherein the first or second parent canola plant is a canola plant of 15RH0612. Further, both first and second parent canola plants can come from the canola 15RH0612. Thus, any such methods using the canola cultivar 15RH0612 are part of this invention: selfing, backcrosses, hybrid production, crosses to populations, and the like. All plants produced using canola 15RH0612 as a parent are within the scope of this invention, including those developed from varieties derived from canola 15RH0612. Advantageously, the canola variety could be used in crosses with other, different, canola plants to produce first generation (F1) canola hybrid seeds and plants with superior characteristics. The cultivar of the invention can also be used for transformation where exogenous genes are introduced and expressed by the cultivar of the invention. Genetic variants created either through traditional breeding methods using 15RH0612 or through transformation of 15RH0612 by any of a number of protocols known to those of skill in the art are intended to be within the scope of this invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions and sub-combinations as are within their true spirit and scope.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application.

Deposit Information

A deposit of the Cargill Incorporated proprietary canola 15RH0612 disclosed above and recited in the appended claims has been made with the American Type Culture Collection (ATCC), 10801 University Boulevard, Manassas, Va. 20110. The date of deposit was Jun. 16$^{th}$2016 and the deposit is intended to meet all of the requirements of 37 C.F.R. Sections 1.801-1.809. The ATCC accession number is PTA-12315. The deposit will be maintained in the depository for a period of 30 years, or 5 years after the last request, or for the effective life of the patent, whichever is longer, and will be replaced as necessary during that period.

I claim:

1. A plant of canola hybrid 15RH0612, or part thereof, representative seed of the hybrid having been deposited under ATCC Accession No. PTA-12315.

2. A method of producing a canola plant comprising a trait, the method comprising introducing a gene conferring a trait into the plant of claim 1.

3. The method of claim 2, wherein the canola plant comprising the trait further comprise a seed having an oil comprising (i) a total saturates of between 4% and 5%; (ii) a linoleic acid content is from 21% to 28%; and (iii) a linolenic acid content is from 2.0% to 3.0%.

4. The method of claim 2, wherein the canola plant comprising the trait further comprises herbicide resistance to an herbicide selected from the group consisting of imidazolinone, sulfonylurea, glyphosate, glufosinate, L-phosphinothricin, triazine, Clearfield, Dicamba, 2,4-D, and benzonitrile.

5. A method of modifying fatty acid metabolism or modifying carbohydrate metabolism of canola hybrid 15RH0612 wherein the method comprises: (a) crossing the plant of claim 1 with a plant of another canola cultivar to produce F1 progeny plants that comprise a nucleic acid molecule encoding an enzyme selected from the group consisting of phytase, fructosyltransferase, levansucrase, alpha-amylase, invertase and starch branching enzyme or encoding an antisense of stearyl-ACP desaturase; and (b) selecting one or more progeny plants that have said nucleic acid molecule to produce selected progeny plants with modified fatty acid metabolism.

6. The method of claim 5, wherein the fourth or higher backcross progeny plants further comprise resistance to Blackleg (*Leptosphaeria maculans*), Fusarium wilt, or White Rust.

7. The method of claim 5, wherein the fourth or higher backcross progeny plants further comprise herbicide resistance to an herbicide selected from the group consisting of imidazolinone, sulfonylurea, glyphosate, glufosinate, L-phosphinothricin, triazine, Clearfield, Dicamba, 2,4-D, and benzonitrile.

8. A method for producing canola oil, the method comprising processing seed harvested from the plant of claim 1 and extracting or pressing the oil from the seed.

9. A method of producing a canola seed, the method comprising growing the plant of claim 1 to produce a subsequent generation of seed and harvesting the subsequent generation of seed.

10. A method for producing a second canola plant or plant part, the method comprising doubling haploid seed generated from the plant of claim 1, thereby producing the second canola plant or plant part.

11. A method for producing a canola plant derived from canola hybrid 15RH0612, the method comprising: crossing the plant of claim 1 with itself or a second plant to produce progeny seed; and growing the progeny seed to produce a plant derived from canola hybrid 15RH0612.

12. A method for cooking or frying comprising cooking or frying food in the oil produced from the method of claim 8.

13. A method of producing a canola plant comprising a trait comprising transforming a plant of canola hybrid 15RH0613, or part thereof, with a transgene, wherein said transgene confers said trait into said plant, wherein said trait is selected from the group consisting of Total Saturates less than 5%, male sterility, herbicide resistance, insect resistance, and resistance to bacterial disease, fungal disease or viral disease, wherein representative seed of the hybrid has been deposited under ATCC Accession No. PTA-12316.

14. A canola plant comprising the trait produced by the method of claim 13, further comprising an oleic acid value of about 65%.

15. The canola plant comprising the trait of claim 13, wherein the herbicide resistance is conferred to an herbicide selected from the group consisting of imidazolinone, sulfonylurea, glyphosate, glufosinate, L-phosphinothricin, triazine, Clearfield, Dicamba, 2,4-D, and benzonitrile.

16. The canola plant comprising the trait of claim 15, wherein the trait further comprises insect resistance and the insect resistance is conferred by a transgene encoding a *Bacillus thuringiensis* endotoxin.

17. The canola plant comprising the trait of claim 15, wherein the trait further comprises resistance to Blackleg, Fusarium wilt, or White Rust.

* * * * *